(12) United States Patent
Yaroslavsky (10) Patent No.: US 11,944,450 B2
(45) Date of Patent: Apr. 2, 2024

(54) SPECTRALLY ENCODED OPTICAL POLARIZATION IMAGING FOR DETECTING SKIN CANCER MARGINS

(71) Applicant: UNIVERSITY OF MASSACHUSETTS, Boston, MA (US)

(72) Inventor: Anna N. Yaroslavsky, North Andover, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 366 days.

(21) Appl. No.: 17/250,855

(22) PCT Filed: Sep. 12, 2019

(86) PCT No.: PCT/US2019/050808
§ 371 (c)(1),
(2) Date: Mar. 12, 2021

(87) PCT Pub. No.: WO2020/056134
PCT Pub. Date: Mar. 19, 2020

(65) Prior Publication Data
US 2021/0251564 A1 Aug. 19, 2021

Related U.S. Application Data

(60) Provisional application No. 62/730,052, filed on Sep. 12, 2018.

(51) Int. Cl.
*A61B 5/00* (2006.01)

(52) U.S. Cl.
CPC ............ *A61B 5/444* (2013.01); *A61B 5/0075* (2013.01); *A61B 5/0077* (2013.01); *A61B 5/7203* (2013.01); *A61B 5/742* (2013.01)

(58) Field of Classification Search
CPC ..... A61B 5/444; A61B 5/0075; A61B 5/0077; A61B 5/7203; A61B 5/742; A61B 5/441
See application file for complete search history.

(56) References Cited

U.S. PATENT DOCUMENTS

2001/0056237 A1* 12/2001 Cane .................... A61B 5/0075
600/475
2016/0066833 A1* 3/2016 Yaroslavsky ........ A61B 5/0077
600/310

FOREIGN PATENT DOCUMENTS

WO 2014165820 A1 10/2014

OTHER PUBLICATIONS

International Search Report and Written Opinion of PCT/US2019/050808, dated Nov. 18, 2019, 15 pages.
(Continued)

*Primary Examiner* — Devin B Henson
*Assistant Examiner* — Jonathan M Haney
(74) *Attorney, Agent, or Firm* — Brake Hughes Bellermann LLP (57) ABSTRACT

Many treatments of skin cancer need an accurate assessment of the margins of the tumor. Spectrally-encoded optical polarization imaging improves upon the demarcation of skin cancer such as keratinocytic carcinomas. When the clinician can outline the clinical boundary of each lesion, surgery and other treatments can be more efficient and effective. Optical images of the lesions are acquired at various wavelengths, then spectrally-encoded. Spectral-encoding of the images minimizes the impact of background pigmentation and vascularization so that the tumor can be accurately visualized.

14 Claims, 5 Drawing Sheets

(56) References Cited

OTHER PUBLICATIONS

Demos, S., et al., "Optical Polarization Imaging", Applied Optics, Jan. 1, 1997, 150-155.

* cited by examiner

SPECTRALLY ENCODED OPTICAL POLARIZATION IMAGING FOR DETECTING SKIN CANCER MARGINS

CROSS REFERENCE TO RELATED APPLICATION

This application is a 35 U.S.C. § 371 National Phase Entry Application from PCT/US2019/050808, filed Sep. 12, 2019, designating the U.S., and claims the benefit of U.S. Provisional Application No. 62/730,052, filed Sep. 12, 2018, the disclosures of which are incorporated herein by reference in their entireties.

BACKGROUND

1. Field

The subject disclosure relates to methods and systems for imaging tumors for improved determination of tumor margins.

2. Background of the Related Art

Keratinocytic carcinoma (KC) is the most common form of cancer in the United States, diagnosed in 3.3 million individuals annually. Surgical removal of the cancerous lesion is the most common form of treatment. Mohs micrographic surgery has been the standard for KC tumor removal for several decades. Intraoperative histologic identification and removal of tumor at the surgical margin yields very high cure rates and helps to preserve normal tissue compared to other techniques.

However, determining the initial dimensions of the first excision stage prior to surgery is challenging and relies on the surgeon's clinical intuition and experience. Even the most experienced surgeons underestimate or miscalculate the clinical margins 35% of the time on average. The inaccurate, initial identification of the tumor margins increases the number of stages needed to clear the tumor, amplifying the cost of and time required for the surgical procedure.

SUMMARY

In view of the above, utilization of advanced imaging strategies can help establish more accurate surgical margins in-situ, which saves time, uses resources effectively, and improves treatment. The subject technology provides such imaging without disrupting the clinical workflow by acquiring data rapidly and producing images that are easy to interpret. The subject technology is also relatively inexpensive. In short, the subject technology provides improved methods and systems for imaging and demarcation of skin cancer and like lesions.

Commercially-available imaging devices for in vivo margin assessment of KCs include reflectance confocal microscopy (RCM) and optical coherence tomography (OCT). While RCM has a very high resolution and can identify individual tumor cells, RCM has small field of view and produces images that are challenging to acquire and interpret without extensive training. OCT can assess larger areas of skin than RCM, but has a lower lateral resolution and cannot discriminate individual tumors cell reliably. Like RCM, OCT requires extensive training for the surgeon to become proficient at image acquisition and interpretation. Both technologies are comparatively slow and expensive. Even though optical polarization imaging (OPI) does not resolve single tumor cells, OPI provides a field of view of several centimeters in real time, adequate imaging depth, and 12-20 µm of lateral resolution. In contrast to other imaging modalities such as RCM and OCT, OPI uses lower incident power densities that are harmless to human skin. OPI technology is relatively simple, inexpensive, yields easy-to-interpret images and does not require extensive training. Therefore, OPI is viable and preferred for preoperative KC margin delineation but other technologies now known and later developed can be effectively deployed in the subject technology.

Additionally, not all skin cancers are operable. Various other treatments may be available such as radiation or drug therapy. It is also helpful to identify the margins of the skin cancer in these circumstances as well. For example, before treatment, accurate identification of the tumor can insure that the radiation covers the tumor for proper dosage while avoiding excessive dosage in unnecessary areas. After treatment, review of the size of the tumor can be used to evaluate the efficacy of treatment such as how much the tumor has shrank post-treatment.

The present disclosure is directed to an instrument for imaging a region of tissue comprising an illuminator for illuminating the region with two wavelengths of light, an imaging detector for generating images of the region based upon the light, and a controller connected to the imaging detector for receiving and storing the images, wherein the images are spectrally-encoded to create spectrally-encoded images that illustrate a collagen structure of the region of the tissue. The images may be gray scale and/or pseudo-colored. Preferably, the controller is further operative to optimize in vivo determination of a boundary of a tumor present in the region by presenting the spectrally-encoded images to a clinician for determining surgical margins around the tumor based upon disruption in the collagen structure. The illuminator can include a polarizer so that the raw images are cross-polarized. The clinician may be a surgeon, radiologist, oncologist or like health care professional.

Another embodiment of the subject technology images a region of tissue to define margins of a tumor in the region. The instrument includes an illuminator for illuminating the region with at least two wavelengths of light, an imaging detector for generating images of the region based upon the at least two wavelengths of light and a controller connected to the imaging detector for receiving and storing the images. The images are spectrally-encoded to create a spectrally-encoded image to exclude effects of background, uneven pigmentation and vascularization for visualizing a collagen structure of the region of the tissue so that disruption of the collagen structure caused by the tumor is determined and, in turn, the margins of the tumor.

Still another embodiment of the present disclosure includes an instrument for imaging a region of tissue having a tumor to minimize an optical effect of melanin and hemoglobin. The instrument includes an illuminator for illuminating the region with 440 nm light and 640 nm light, an imaging detector for generating raw images of the region based upon the 440 nm light and the 640 nm light, a polarizer for creating cross-polarized images, and a controller connected to the imaging detector for receiving and storing the images. The controller encodes a first cross-polarized raw image at 440 nm light with a second cross-polarized raw image at 640 nm light to create a corrected image according to a formula as follows:

$$PXL_{i,j} = \beta \times PXL_{i,j}^{440\,nm\,\perp} - PXL_{i,j}^{640\,nm\,\perp} + 1{,}000 \times \Delta \qquad (1)$$

where: PXL is an abbreviation for pixel value; i is the pixel number in x-direction; j is the pixel number in y-direction; $PXL_{i,j}$ are pixel values of the corrected image, $PXL_{i,j}^{440\ nm}$ are pixel values of the first cross-polarized raw image; $PXL_{i,j}^{640\ nm}$ are pixel values of the second cross-polarized raw image; β is a first constant defined as $$\beta = \frac{PXL_{mean}^{640\ nm}}{PXL_{mean}^{440\ nm}};$$

and Δ is a second constant defined as:

$$\Delta = \frac{PXL_{mean}^{640\ nm} - PXL_{region,mean}^{640\ nm}}{PXL_{mean}^{640\ nm}}$$

where: $PXL_{mean}^{640\ nm}$ is a mean pixel value of the second cross-polarized raw image; $PXL_{mean}^{440\ nm}$ is a mean pixel value of the first cross-polarized raw image; and $PXL_{region,\ mean}^{640\ nm}$ is an average pixel value of a sub-region in the second cross-polarized raw image that is located at a distance from the tumor. Typically, the sub-region exhibits a higher pigmentation as compared to other image pixels and/or a higher vascularization as compared to other image pixels. The corrected image can be presented in gray scale and/or pseudo-colored. Preferably, pseudo-colored corrected images have pixels with normalized intensity ≤40% corresponding to a maximal disruption of a collagen network of the region are colored black and purple. In another embodiment, a 20% threshold is applied. Pixels corresponding to normal collagen are represented are colored ranging from blue to white. Preferably, the controller presents the corrected image for visual review by an operator to assess margins of the tumor based on examining a lateral spread of collagen disruption prior to surgery.

As can be seen, the subject technology improves upon what was previously known by taking into account and excluding such things as pigmentation and vascularization of tissue, as well as possible impacts of the uneven illumination, which allows for unbiased and quantitative assessment of the collagen structure.

It should be appreciated that the subject technology can be implemented and utilized in numerous ways, including without limitation as a process, an apparatus, a system, a device, a method for applications now known and later developed such as a computer readable medium and a hardware device specifically designed to accomplish the features and functions of the subject technology. These and other unique features of the system disclosed herein will become more readily apparent from the following description and the accompanying drawings.

BRIEF DESCRIPTION OF THE DRAWINGS

The original filing of the subject application includes color photographs as part of the drawings and such is within the disclosure of the subject application. So that those having ordinary skill in the art to which the disclosed system appertains will more readily understand how to make and use the same, reference may be had to the following drawings.

DETAILED DESCRIPTION OF PREFERRED EMBODIMENTS

The subject technology overcomes many of the prior art problems associated with accurately determining margins of skin cancer such as for preoperative delineation of keratinocytic carcinoma (KC) boundaries or pre- and post-treatment of inoperable skin cancer. The advantages, and other features of the systems and methods disclosed herein, will become more readily apparent to those having ordinary skill in the art from the following detailed description of certain preferred embodiments taken in conjunction with the drawings which set forth representative embodiments of the present invention and wherein like reference numerals identify similar structural elements. It is understood that references to the figures such as up, down, upward, downward, left, and right are with respect to the figures and not meant in a limiting sense.

In brief overview, the subject optical polarization imaging (OPI) technology can be used for the determination of the margins of any skin lesion or cancer. The OPI technology is particularly useful for preoperative delineation of keratinocytic carcinoma (KC) boundaries such as in Patent Cooperation Treaty Patent Application No. PCT/US18/25487 entitled INSTRUMENTS AND METHODS FOR IMAGING COLLAGEN STRUCTURE IN VIVO filed on Mar. 30, 2018 (the '487 application), which is incorporated herein by reference. The '487 application is based on dermal collagen disruption being an accurate marker for the presence of tumor. Collagen disruption in the papillary dermis in the presence of skin cancer or other lesions can be visualized by OPI at submillimeter resolution. Spectrally-encoded OPI further improves the visualization of collagen disruption by minimizing the optical impact of endogenous chromophores in the skin.

Figure 1:
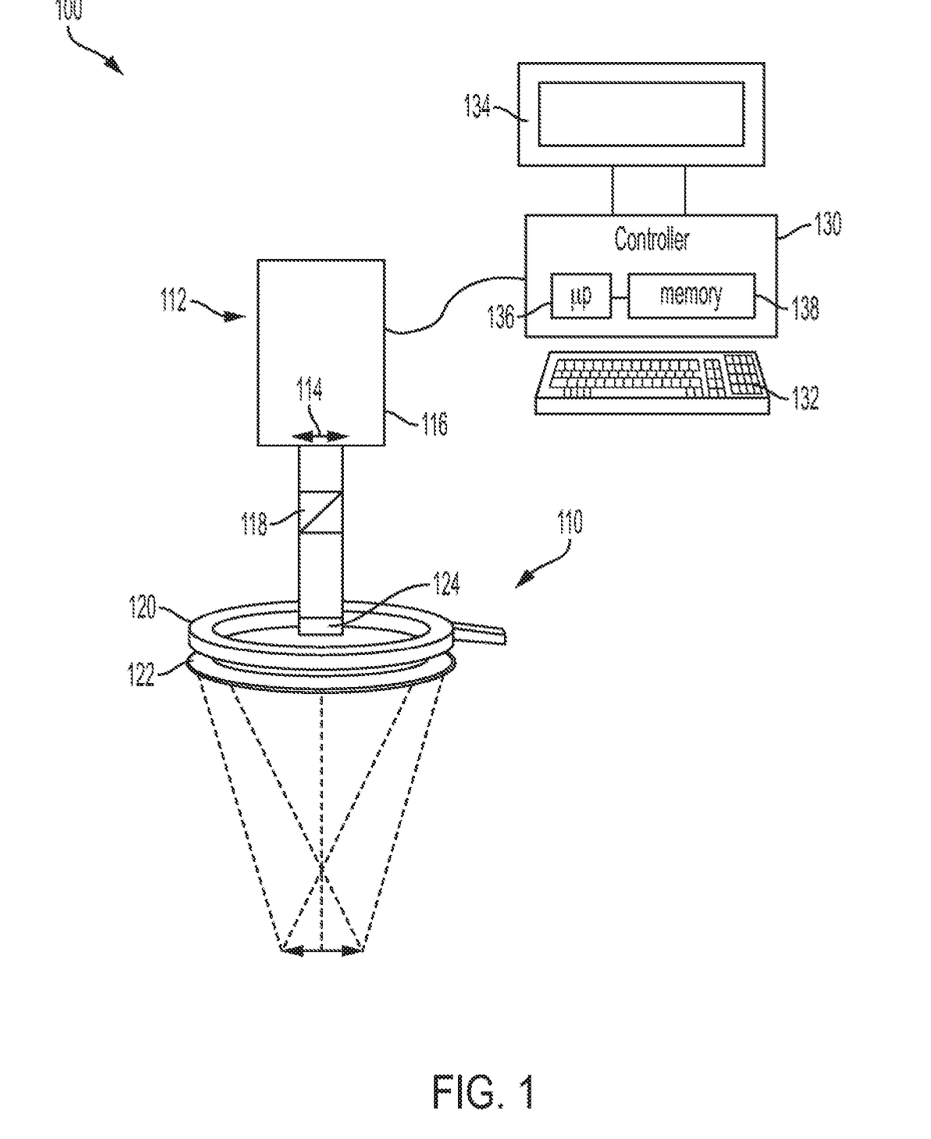
FIG. 1 is a schematic illustration of a wide-field imaging instrument in accordance with the subject disclosure.

Referring now to FIG. 1, a schematic view of a light delivery and detector element assembly 10 of a wide-field imaging instrument 100 is shown. The instrument can generate images of collagen structures of the skin with intact epidermis. The OPI system 110 includes a camera housing 112 in which a detector 116 such as CCD or CMOS camera is positioned to receive a cross-polarized image 114 from polarizing beamsplitter 118 and a lens 124. Illumination is provided by an LED ring 120, for example, that can delivers polarized light using a linear polarizer 122, onto a field of view 126 on a tissue surface. The illumination may be any wavelength. Wavelengths of approximately 440 nm light, approximately 550 nm light, approximately 590 nm light, approximately 640 nm light, light in a range of 410 nm to 440 nm, light in a range of 570 nm to 590 nm, and light in a range of 640-730 nm are particularly useful because of the absorption or other interaction with skin chromophores such as melanin, hemoglobin and blood. The OPI system 110 can be integrated into a handheld unit (not shown) of a portable diagnostic imaging instrument. The housing 112 includes a detector 116 that collects images from an aperture for sending image data over cable or wireless connection to a controller 130.

The controller 130 may be a typical computer with a keyboard 132 and monitor 134 running application specific software or an application specific device. The controller 130 has a data processor 136 working with memory 138 for storing images and instructions to accomplish the activity envisioned in the subject disclosure. Images and data can be displayed on the monitor 136, or sent via wireless or wired connection over a network such as the Internet. In another embodiment, the controller is simply an application specific printed circuitry board (ASIC PCB). Storing images is particularly useful so that a clinician can compare images over time periods that correspond to various treatments, which may be lengthy.

The methods, processes and the like described herein illustrate structure and/or logic of the present technology, possibly as embodied in an ASIC PCB coupled to or part of a controller having computer program software for execution on a digital processor, microprocessor and the like. Those skilled in the art will appreciate that these methods and processes may illustrate the structures of the computer program code elements, including logic circuits on an integrated circuit, that function according to the present technology. As such, the present technology may be practiced by a machine component that renders the program code elements in a form that instructs a digital processing apparatus and associated components to perform a sequence of function steps corresponding to those shown and described herein.

The OPI system 110 generates narrowband linearly polarized light. Preferably, the wavelength can be adjusted to match a depth of the collagen structure according to a location of the region on the patient or to provide a clear image. The wavelength is typically in a range of 350 nm to 750 nm and, more narrowly in the range of 410 nm to 730 nm. Most preferably, the wavelength has a FWHM of up to 20 nm. The OPI system 110 also functions without use of a contrast agent. The OPI system 110 may use light that is monochromatic, typically blue.

In one embodiment, the OPI system 110 generates narrowband linearly polarized light anywhere in a range of 400 nm to 730 nm (FWHM=10 nm) for skin illumination. These illumination ranges are representative and the subject technology can also utilize wavelengths outside this range. The LED ring 120 can be a fiber optic ring illuminator from Edmund Optics of Barrington, NJ for directing light onto the skin. Cross-polarized reflectance images ar acquired using a 12-bit CCD camera from Coolsnap Monochrome Photometrics, Roper Scientific of Tucson, Ariz. The 12-bit CCD camera 116 includes a 0.3× lens from Rodenstock Photo Optics of Feldkirchen, Germany).

In one embodiment among other things, the 440 nm wavelength generates images that visualize the dermal collagen structure, the 550 and/or 590 nm wavelength generates images that visualize the blood while the 640 nm wavelength generates an image that displays the blue surgeon's marker used to outline clinical borders of the lesion. The camera 116 may be attached to an articulating arm from Manfrotto of Upper Saddle River, N.J. The articulating arm allows flexible positioning on the subjects' skin. A spacer (not shown) between the camera and the skin ensures proper focusing. The OPI system 110 preferably provides a 4 cm$^2$ field of view and lateral resolution of approximately 13 μm. The imaging depth varies with the wavelength. For example, the imaging depth varies from about 115 μm to about 300 μm, at 440 nm or 640 nm, respectively. Light power density at the skin surface ranges between 0.2-0.6 mW/cm$^2$, which is below the maximum permitted skin and ocular exposures set by American National Standards Institute (ANSI).

Use of the OPI system 110 in accordance with the subject technology does not affect current standard treatment practices such as Mohs surgery, chemical treatment or radiation. For example, the clinician can use his own initial markings and revise the markings based on the images as the starting point for Mohs surgery, radiation, chemical treatment and like. The following examples relate to Mohs surgery for illustration. Prior to imaging, the lesion should be cleansed with isopropyl alcohol. The surgeon outlines the clinical border of the excision using a sterile purple marker and digital photographs of the lesion are taken for reference. A transparent coupling gel is applied to the skin and the OPI system 110 is positioned to image the cancerous lesion. Preferably, the imaging is controlled using MetaMorph software from Molecular Devices of Sunnyvale, Calif. The entire imaging procedure requires less than 2 minutes. The optical polarization images can be viewed in real-time or as individual frames after imaging. As needed or desired, the raw frames are processed in MetaMorph using a low pass filter to reduce noise. Following imaging for guidance and marking of the lesion, surgical excision of the tumor is performed using the standard Mohs technique based on the surgeon's assessment of the margins and the imaging analysis.

The subject technology uses the disruption of collagen as a marker for the presence of tumor. Collagen degradation identified by the OPI system 110 in accordance with the subject technology is an excellent marker for tumor presence. Collagen types I and III form a stereotypical net-like structure within the papillary dermis of normal skin. Tumor cells, including basal cell carcinoma (BCC) and KC, are associated with the expression and secretion of collagenases and gelatinases, enzymes that lead to the proteolysis of fibrillar collagens. In an analogous way in which enzyme-linked antibodies increases the sensitivity of detecting bound antibodies, tracking the activity of tumor-associated collagenase helps increase the sensitivity of localizing tumor. A single secreted molecule can enzymatically act on many collagen molecules and disrupt the normal collagen structure. As these secreted enzymes diffuse around the tumor cells, the secreted enzymes mark out a zone within which the tumor is likely to be present. However, skin chromophores such as blood, melanin, hemoglobin and the like interfere with clearly imaging the collagen structure. The subject technology employs spectral-encoding to reduce the impact of skin chromophores so that tumors can be more clearly identified in the resulting images.

For visualization of cancer using collagen disruption, the OPI system 110 implements multi-wavelength, rapid (approximately 1-3 seconds) imaging methods and spectral-encoding data processing algorithms. As demonstrated in FIG. 2 and discussed below, the OPI system 110 minimizes the impact of melanin and hemoglobin on the imaging results and corrects for major operator-induced artifacts such as non-uniform skin illumination.

Normal skin contains collagen that exhibits high reflectance in the 440 nm images, whereas tumors interrupt the collagen network and reduce the amount of reflected light. Skin chromophores, such as melanin and hemoglobin, present in epidermis and dermis, respectively, also strongly scatter and absorb light. The presence of skin chromophores in the field of view reduces the reflected signal and adversely affects the image quality by mimicking the disrupted collagen network.

To minimize the optical effect of skin chromophores (e.g., melanin and hemoglobin) images are encoded using spectrally-dependent properties of melanin and hemoglobin. In one embodiment, the following formula (formula (1)) is applied:

$$PXL_{i,j} = \beta \times PXL_{i,j}^{440\ nm\ \perp} - PXL_{i,j}^{640\ nm\ \perp} + 1{,}000 \times \Delta \quad (1)$$

where PXL is an abbreviation for pixel value, i is the pixel number in x-direction and j is the pixel number in y-direction. $PXL_{i,j}$ are pixel values of the corrected image, $PXL_{i,j}^{440\ nm}$ are pixel values of the cross-polarized image acquired at 440 nm, and $PXL_{i,j}^{640\ nm}$ are pixel values of the cross-polarized image acquired at 640 nm.

Constants $\beta$ and $\Delta$ are defined as:

$$\beta = \frac{PXL_{mean}^{640\ nm}}{PXL_{mean}^{440\ nm}} \quad (2)$$

$$\Delta = \frac{PXL_{mean}^{640\ nm} - PXL_{region,mean}^{640\ nm}}{PXL_{mean}^{640nm}} \quad (3)$$

where $PXL_{mean}^{640\ nm}$ is the mean pixel value of the 640 nm image, $PXL_{mean}^{440\ nm}$ is the mean pixel value of the 440 nm image, and $PXL_{region,\ mean}^{640\ nm}$ is the average pixel value of a region in the 640 nm image that is located at a distance from the tumor, which exhibits higher pigmentation or vascularization as compared to other image pixels. The distance may be selected by the operator before or after review of the images and subsequent images may be acquired. Alternatively, the controller 130 may use artificial intelligence to determine a location in a healthy region. The controller 130 may apply a threshold value, such as 40% to determine an acceptable location.

Preferably, the resulting image is pseudo-colored for ease of interpretation with pixels with normalized intensity ≤20% corresponding to the maximal disruption of the collagen network being colored black and purple. Pixels corresponding to normal collagen are represented by colors ranging from blue to white. Margin assessments can be determined by examining the lateral spread of collagen disruption evident in the spectrally-encoded, pseudo-colored images.

From using the subject technology, it is recommended to use 440 nm and 640 nm to pre-operatively image KCs. To optimize visualization of the cancer lesions, it is effective to use spectral-encoding of the experimental skin images, acquired at 440 nm, using the images of the same lesion acquired at 640 nm. This approach takes into account the underlying wavelength-dependent, optical properties of the major skin chromophores, specifically melanin and hemoglobin.

In particular, the chromophores of melanin and hemoglobin exhibit strong absorption at both 440 and 640 nm. However, lower scattering at 640 nm yields deeper light penetration. As a result, the 640 nm images capture a thicker section of skin and do not resolve collagen bundles in the papillary dermis well. A pixel-by-pixel application of formula (1) to the experimental skin images acquired at 440 and 640 nm effectively minimizes the impact of melanin-related pigmentation and hemoglobin-related vascularization on the images, thereby revealing the fibrillar collagen network.

Figure 2:
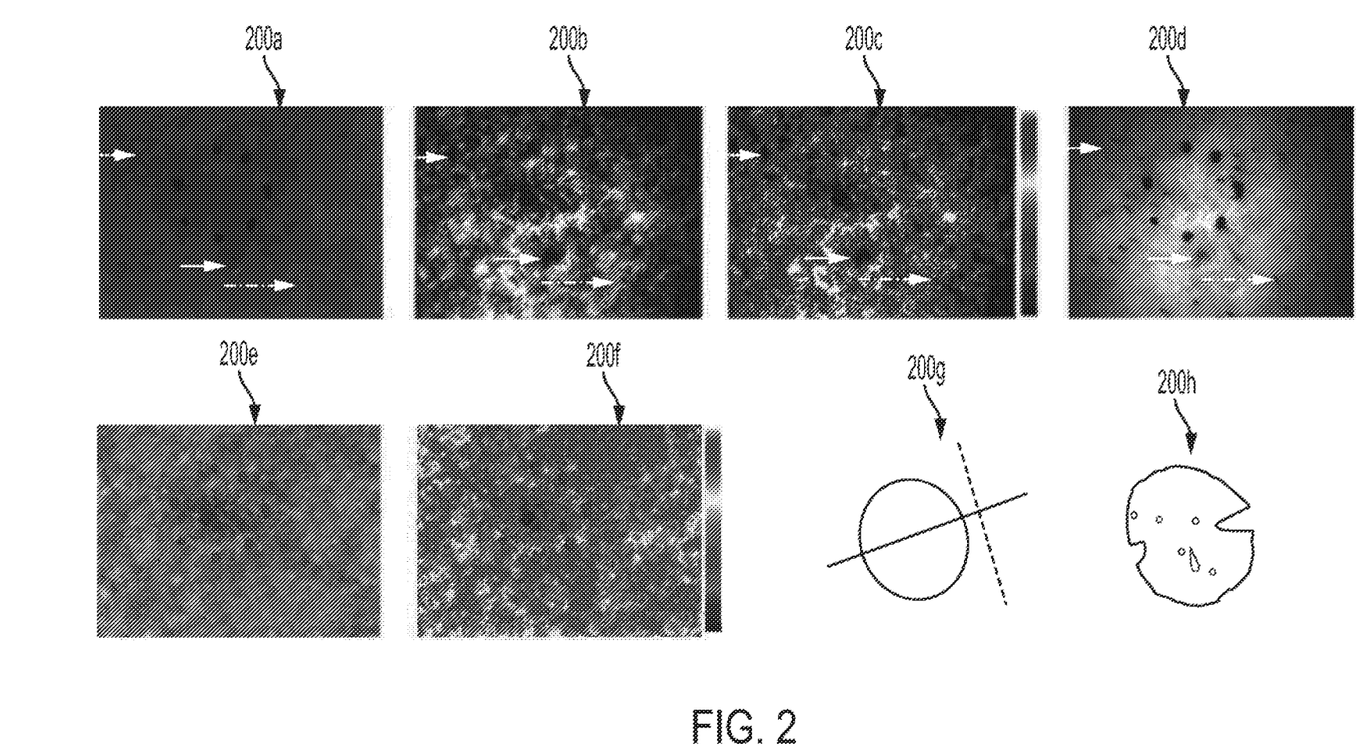
FIG. 2 is a series of images for demonstrating the subject technology.

For example, in FIG. 2, a series of images 200a-h are shown for demonstrating the subject technology. The field of view in images 200a-f is 2.2×1.6 cm² and the lateral tumor size is 1.0×1.0 cm². The images 200a-h include the raw optical image and the spectrally-encoded optical image of a nodular BCC on the cheek of a patient prior to Mohs surgery. Image 200a is a digital photograph of the lesion outlined with surgical marker. Solid arrows point to pigmented spots and dashed arrows to blood vessels that happen to be outside the region marked with the surgical marker. The dash and dot arrow indicates a hair shaft that is also outside the region encircled by the surgical marker. The region within the surgical marker is slightly darker, which was visible to the surgeon.

Images 200b, 200c show gray scale and pseudo-colored raw optical images of a lesion acquired at 440 nm, respectively. It can be appreciated that pigmented macules and blood vessels significantly reduce reflectance signal from the respective pixels. Melanin containing hairs are also prominent in both images 200b, 200c. Image 200b is a largely speckled grey scale looking region in which it is difficult to determine features and the associated boundaries. Image 200c, being in color, ranges from white to black so that relatively more contrast is present but still, features and the associated boundaries are difficult to determine.

Image 200d shows the raw image of the lesion imaged at 640 nm where, in addition to pigmented macules, blood vessels and hair, the surgical markings can be clearly seen as dark against a light grey background. Images 200e, 200f present spectrally encoded gray-scale and pseudo-colored images of the lesion. Images 200e and 200f are superimposed with the surgeon's marker shown in magenta. Image 200e is again a grey scale image with a darkly contrasted area within the surgeons marking, which compared to image 200b, makes for much easier and clearer visual recognition of the margins on the lesion (i.e., the darkly contrasted area within the surgeons marking). Similarly, image 200f is pseudo-colored image with a dark blue and purple area within the surgeons marking on a lighter blue, green, yellow and pink background, which compared to image 200c, makes for much easier and clearer visual recognition of the margins on the lesion (i.e., the dark blue and purple contrasted area within the surgeons marking).

Comparison of the spectrally-encoded images 200e, 200f with the raw images 200b, 200c demonstrates that the spectral encoding method strongly reduces the impact of background blood and melanin. The Mohs map and histopathology, presented in images 200g, 200h, indicate that the excision margins were negative for cancer after the first surgical stage. Thus, the optical images 200e, 200f correlate well with the Mohs map and histopathology for use before surgery. It is worth pointing out that this technique also corrects for operator introduced artifacts, such as uneven illumination of the imaging field. After raw image subtraction (see formula (1)), the illumination gradient, evident in images 200b-d, is not present in images 200e, 200f.

Figure 3:
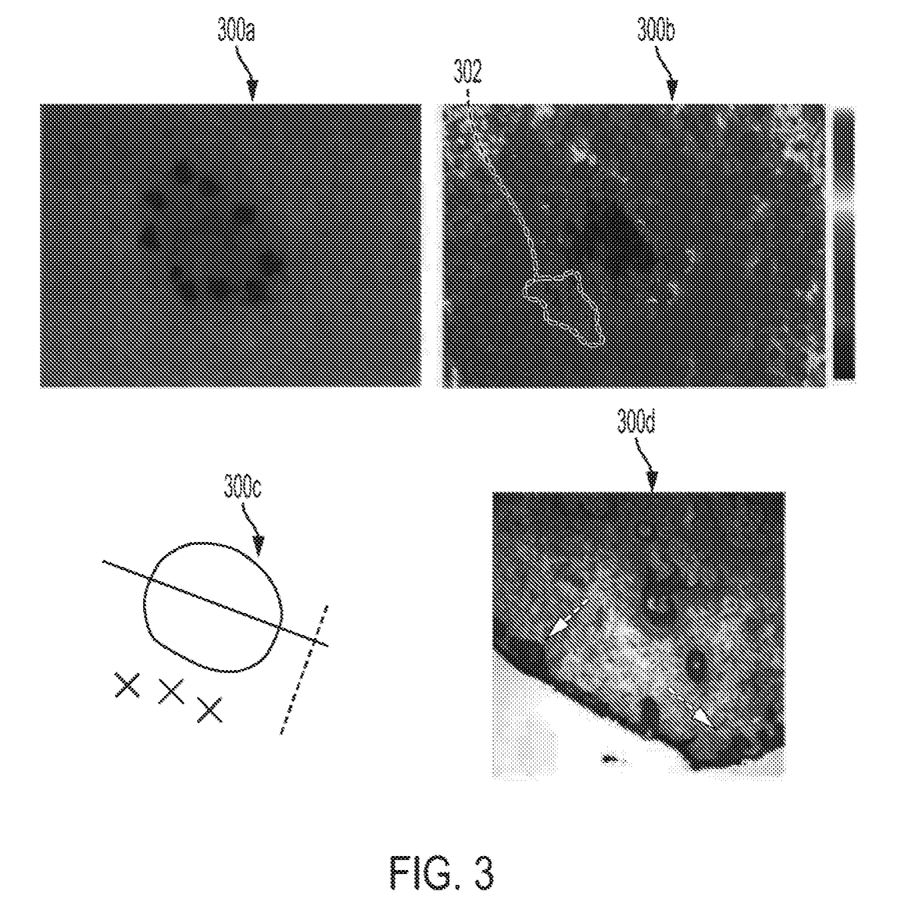
FIG. 3 is another series of images for demonstrating the subject technology.

Another representative example of a series of images 300a-d of a nodular BCC lesion is shown in FIG. 3. The images 300a, 300b were taken preoperatively. The BCC lesion was positive after the first stage and required two stages of Mohs surgery. The preoperative image 300a shows the presumptive boundaries of the tumor as marked by the surgeon with purple marker using only his clinical intuition (e.g., the traditional approach). As can be seen, the skin is fairly uniform except for a darker area encircled by the surgeons marks. The lateral tumor size is approximately 1.1×0.9 cm² with a field of view of 2.2×1.6 cm².

Referring now in particular to the preoperative pseudo-colored spectrally-encoded OPI image 300b, the OPI image 300b is superimposed with the same surgeon's marks, shown in magenta. Black and purple colors represent regions with low reflectivity due to the distortion of the collagen network. Blue, green, yellow and red colors represent normal collagen structure. As can be seen, the black and purple colors are largely within the surgeon's marker except for a one region 302. The blue, green, yellow and red colors are predominant from the surgeon's marker outward. Thus, the OPI image 300b reveals that at the left lower margin, there is collagen disruption region 302 outside the boundaries of the lesion marked by the surgeon. The Mohs map and histology are shown in images 300c, 300d, respectively. Intraoperative histopathology confirms the presence of tumor at the lower left margin of the excision, coinciding with the area 302 of collagen disruption identified by review of the OPI image 300b. As would be appreciated by those of ordinary skill in the pertinent art, the OPI image 300b can provide pre-operative guidance to the surgeon for improved marking of the tumor region.

Figure 4:
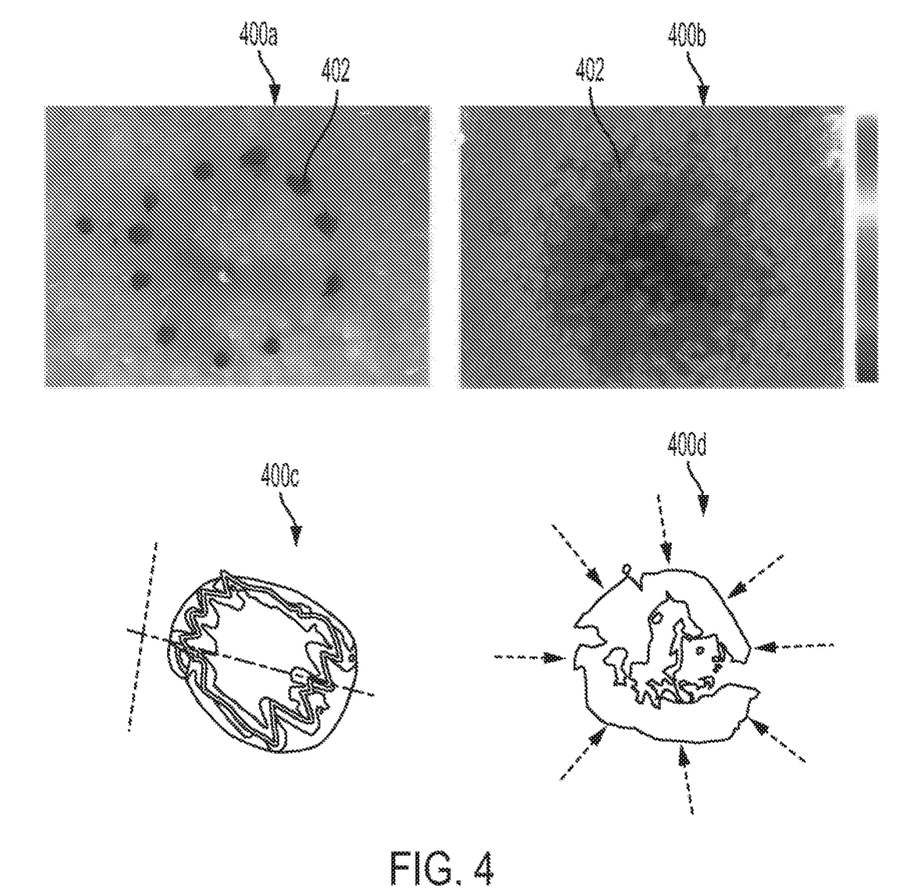
FIG. 4 is still another series of images for demonstrating the subject technology.

Referring now to FIG. 4, another series of images 400a-d are illustrated that related to a nodular BCC that required 5 stages of Mohs surgery. The field of view in images 300a-d is 2.2×1.6 cm² and the lateral tumor size is approximately 1.8×1.7 cm². The clinical photograph image 400a has purple presurgical markings 402 that demonstrate that the surgeon's best guess at the tumor margins. Again, the skin is fairly typical looking except for a darker red area within the surgeon markings 402. The OPI system 110 generates the spectrally-encoded OPI image 400b that shows collagen distortion represented by purple and black pixels, superimposed with the surgeon's markings 402 in magenta. As can be seen in image 400b, the collagen disruption (e.g., the purple and black area) extends beyond the entire marked area within the surgeon markings 402, with blotches of purple and black even likely extending outside of the 4 cm² field of view as seen in the top and bottom parts of the image. The area outside the collagen disruption shows as blue, green and yellow as distance progresses from the center of the tumor. The histopathology image 400d and the corresponding surgical map image 400c confirmed that residual tumor surrounded the lateral margin of the excised Mohs section. In image 400d, subclinical extension of the lesion is identified with red arrows in histopathology. Thus, these exemplary images 400a-d demonstrate how the OPI system 110 provides useful information that could help a surgeon to generate a more accurate margin before the first excision for an improved surgical process.

Figure 5:
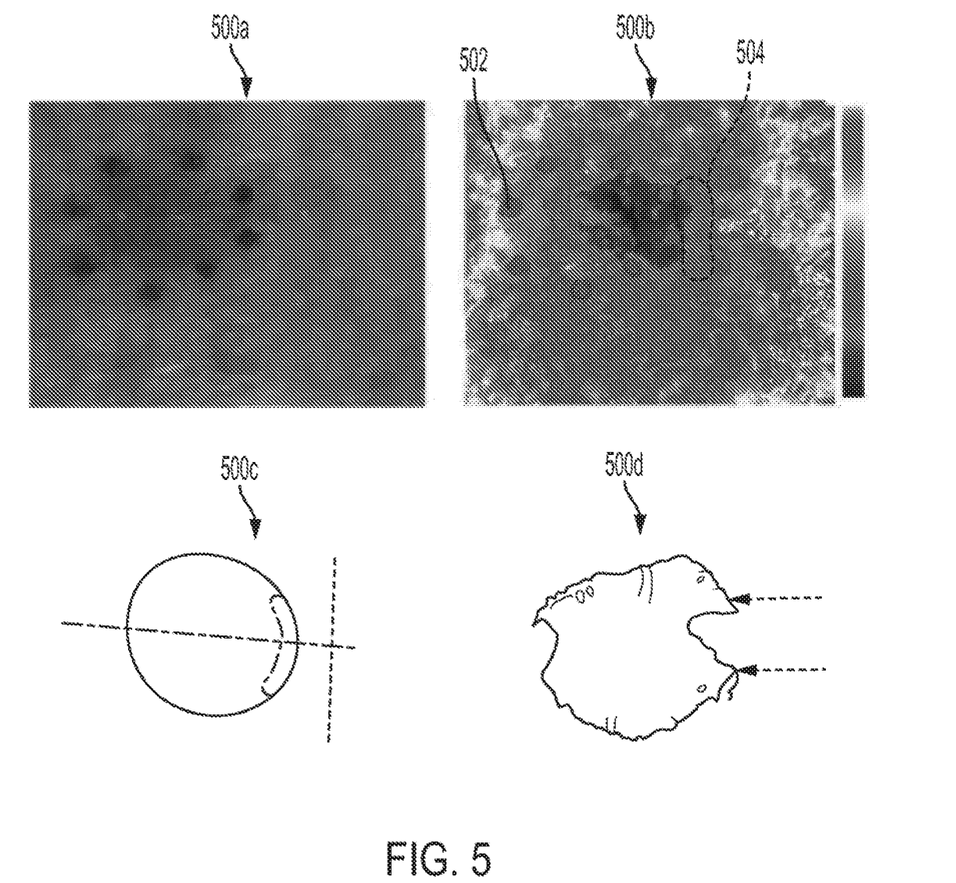
FIG. 5 is yet another series of images for demonstrating the subject technology.

Still another representative example of a series of images 500a-d related to squamous cell carcinoma (SCC) in situ is shown in FIG. 5. The images 500a, 500b were taken preoperatively. The field of view in images 500a-d is 2.2× 1.6 cm² and the lateral tumor size is approximately 1.0×0.8 cm². During subsequent surgery, this SCC was positive after the first stage. Image 500a is a preoperative photograph of the lesion with surgeon's markings 502. Uneven background pigmentation of the skin surrounding the lesion and multiple telangiectasias make visual delineation of the margins challenging. Still, the surgeon's markings are fairly oval around a relatively uniformly darker area.

Image 500b is a spectrally-encoded OPI of the lesion that reveals damaged collagen extending to the right side in area 504 beyond the overlaid surgeon's markings 502 (shown with magenta dots). Image 500b includes a defined purple and black area (e.g., the collagen disruption area) slightly misaligned with the surgeon's marking 502. Image 500b progresses from purple to blue to green to yellow to red going outward from the purple and black area. The intraoperative Mohs map image 500c and the histopathology image 500d confirm that cancer was present at the right margin of the excision. In short, image 500b would have allowed the surgeon to see the collagen disruption area as purple and black, and draw a more accurate mark to help with the removal process.

In addition to the results discussed herein, many other subjects between forty-three and ninety-one years old were studied. Using the OPI system and teachings herein more accurately predicted subclinical extension of tumor beyond the marked surgical boundary using solely the surgeon's traditional intuition. Based upon evaluation using intraoperative histopathology, use of the subject technology was successful when collagen disruption (i.e. NMSC lesion) was absent or confined within the boundaries of the surgical marker. That is, there was concordance between collagen disruption being confined within surgical marking boundary and tumor being absent on histopathological analysis in the Mohs lab. For cases requiring additional excision beyond the surgical marking, the OPI assessment of the subject technology was considered successful when the image analysis identified collagen disruption extending radially beyond the surgical marking boundary in the same topographic region where tumor was mapped using Mohs microscopic tissue analysis. As such, incorporating the subject technology using the information about collagen disruption obtained using the OPI system 110 into the presurgical determination of surgical margins will decrease the need for multiple Mohs stages. In addition, it may narrow the intersurgeon variability in average Mohs layer per case that has been recently reported.

Additional approaches are very effective. For example, additional wavelengths may be used such as a wavelength matched to the absorption peak of blood or the relevant skin chromophores that is interfering with good imaging. Many different wavelengths can be used to capture images so that the controller 130 can process and present many different images for review or utilize artificial intelligence to determine an optimal image set for review. It is envisioned that depending upon the various structure and skin chromophores, various combinations of wavelengths will generate the best images.

In one embodiment, co- and cross-polarization images in the vicinity of 410 nm-440 nm, 570 nm-590 nm, 640-730 nm are acquired. The acquired images are spectrally encoded to exclude the background, as well as effects of uneven pigmentation and vascularization on the resulting image of collagen network and collagen network deterioration and disruption caused by ageing and diseases, such as for example cancer. The following formula (4) is useful for generating images in accordance with the subject technology.

$$PXL_{i,j}^{DIV} = \frac{\alpha \times PXL_{i,j}^{440\ nm\perp}}{PXL_{i,j}^{640\ nm\perp}} + 1,000 \times \delta \tag{4}$$

where $PXL_{i,j}^{DIV}$ is the pixel values of the spectrally encoded image, $PXL_{i,j}^{640\ nm\ \perp}$ is the pixel value of the cross-polarized image acquired at 640 nm, $PXL_{i,j}^{440\ nm\ \perp}$ is the pixel value of the cross-polarized image acquired at 440 nm, i is the number of a pixel in the x-direction, j is the number of pixel in the y-direction, α equals $$\alpha\ \text{equals}\ \frac{PXL_{mean}^{640\ nm\perp}}{PXL_{mean}^{440\ nm\perp}},$$

$$\delta = \frac{PXL_{mean}^{640\,nm\perp} - PXL_{region,mean}^{640\,nm\perp}}{PXL_{mean}^{640\,nm\perp}},$$

$PXL_{mean}^{640\,nm\,\perp}$ is the mean pixel value of the image acquired at 640 nm $PXL_{mean}^{440\,nm\,\perp}$ is the mean pixel value of the image acquired at 440 nm, and $PXL_{region,\,mean}^{640\,nm\,\perp}$ is the average pixel value of the region exhibiting higher pigmentation/vascularization as compared to the other image pixels.

Formula (5) below is another formula useful for generating images:

$$PXL_{i,j}^{SUB} = PXL_{i,j}^{640\,nm\,\perp} - \beta \times PXL_{i,j}^{440\,nm\,\perp} + 1,000 \times \delta, \quad (5)$$

where $PXL_{i,j}^{SUB}$ is the pixel values of the spectrally encoded image, $PXL_{i,j}^{640\,nm\,\perp}$ is the pixel value of the cross-polarized image acquired at 640 nm, $PXL_{i,j}^{440\,nm\,\perp}$ is the pixel value of the cross-polarized image acquired at 440 nm, i is the number of a pixel in the x-direction, j is the number of pixels in the y-direction, $$\beta = \frac{PXL_{mean}^{640\,nm\perp}}{PXL_{mean}^{440\,nm\perp}},$$

$$\delta = \frac{PXL_{mean}^{640\,nm\perp} - PXL_{region,mean}^{640\,nm\perp}}{PXL_{mean}^{640\,nm\perp}},$$

$PXL_{mean}^{640\,nm\,\perp}$ is the mean pixel value of the image acquired at 640 nm $PXL_{mean}^{440\,nm\,\perp}$ is the mean pixel value of the image acquired at 440 nm, and $PXL_{region,\,mean}^{640\,nm\,\perp}$ is the average pixel value of the region exhibiting higher pigmentation and/or vascularization as compared to the other image pixels.

The following formulas (6-9) below are additional useful formulas for generating images. It is noted that by changing the signs in the formulas, inverse images may be created. It is envisioned that such inverse images are also useful to generate and review. Formulas (6-13) utilize some of the same constants as above so that repetition is not needed. Constants $\alpha$, $\beta$, $\varepsilon$, $\eta$, and $\delta$ are selected based on the amplitude of the histograms of the experimental images. Constants $\alpha$, $\beta$, $\varepsilon$, $\eta$, and $\delta$ may also be selected based on the absolute reflectance of the skin determined by introducing the calibrated reflectance reference into the imaging field of view.

Spectrally Encoded Image=($\alpha\times$Cross Image at ~400 nm)/(Cross Image at ~600+$\delta$) (6)

Spectrally Encoded Image=$\beta\times$Cross Image at ~600 nm Cross–Image at ~400 nm+$\delta$ (7)

Spectrally Encoded Image=[$\varepsilon\times$($Co$–Cross Image at ~400 nm)]/[($Co$–Cross Image at ~600 nm)+$\delta$] (8)

Spectrally Encoded Image=$\eta\times$([$Co$–Cross Image at ~600 nm]–[$Co$–Cross Image at ~400 nm])+$\delta$ (9)

Additional specific formulas may be utilized to account for specific skin chromophores. For example, formulas (10-13) below account for the blood or melanin content of skin mainly by adjusting the wavelength.

Spectrally Encoded Image=$\alpha\times$Cross Image at ~500 nm/Cross Image at ~600 nm+$\delta$ (10)

Spectrally Encoded Image=$\beta\times$Cross Image at ~600 nm–Cross Image at ~500 nm+$\delta$ (11)

Spectrally Encoded Image=$\varepsilon\times$($Co$–Cross Image at ~500 nm)/($Co$–Cross Image at ~600 nm)+$\delta$ (12)

Spectrally Encoded Image=$\eta\times$([$Co$–Cross Image at ~600 nm]–[$Co$–Cross Image at ~500 nm])+$\delta$ (13)

In view of the above, it can be seen that the subject technology allows a clinician to identify skin lesions and characterize their lateral dimensions in a more objective manner. The collagen structure varies between normal and cancerous skin. It is noteworthy in that the subject technology does not require use of any exogenous contrast agents. The subject disclosure significantly improves on the prior art by allowing: 1) Increased objective accuracy of detecting and delineating lesions; 2) full lesion removal or treatment based upon improved demarcation of the margins; 3) reduction in the number of stages in Mohs micrographic surgery, thus reducing cost and procedure time; 4) Minimization of the volume of intact healthy tissue removed during surgery, thus decreasing the time and improving aesthetic outcome; and 5) Rapid, real-time image acquisition which will not delay treatment.

In other words, optical polarization imaging (OPI) with spectral-encoding is a non-invasive and rapid imaging modality that highlights the relevant structure (e.g., dermal collagen) while excluding other structure (e.g., skin chromophores). When this OPI is used pre-treatment with multiple wavelengths to perform imaging of NMSCs, OPI can provide critical guidance for surgeons, oncologists and clinicians about to utilize treatment for KC, BCC, lymphoma and the like. OPI allows efficient planning by identifying tumor extension beyond visibly involved skin, thus reducing the necessity for additional treatments and the potential for recurrence. The subject technology is an in vivo nonintrusive collagen-imaging method to diagnose skin diseases. Further, the subject technology is also useful for imaging healthy skin. Such imaging may allow for evaluation of various treatments and monitoring of treated healthy areas.

While the present invention has been described here in conjunction with certain preferred embodiments, a person with ordinary skill in the art, after reading the foregoing specification, can effect changes, substitutions of equivalents and other alterations to the instruments and methods described herein. Each embodiment described above can also have included or incorporated therewith such variation as disclosed in regard to any and all of the other embodiments. Thus, it is intended that the scope of the claims granted herewith be limited in breadth only by definition as defined in the specification and appended claims and any equivalents thereof.

What is claimed is:

1. An instrument for imaging a region of tissue including a tumor, the instrument comprising:
    an illuminator for illuminating the region with two wavelengths of light;
    an imaging detector for generating images of the region based upon the two wavelengths of light; and
    a controller connected to the imaging detector for receiving and storing the images, and for creating spectrally-encoded images that illustrate a collagen structure of the region of the tissue,
    wherein each of the images generated by the imaging detector includes a respective set of pixels, and wherein creating spectrally-encoded images includes (i) multiplying a cross-polarized image of the region based on a first wavelength by a first value to produce a first term, (ii) adding a cross-polarized image of the region based on a second wavelength to the first term to produce a combined image, and (iii) adding a second value to the combined image to produce the spectrally-encoded image, wherein the first value is a normalizing value calculated from a mean pixel value of the cross-polarized image of the region based on the first wavelength and a mean pixel value of the cross-polarized image of the region based on the second wavelength;

wherein the second value is a normalizing value calculated from a mean pixel value of the cross-polarized image of the region based on the second wavelength and a mean pixel value of a subset of pixels of the cross-polarized image of the region based on the second wavelength, the subset corresponding to a non-tumor sub-region;

wherein the two wavelengths of light are selected from the group consisting of: approximately 440 nm light; approximately 550 nm light; approximately 590 nm light; approximately 640 nm light; light in a range of 410 nm to 440 nm; light in a range of 570 nm to 590 nm; and light in a range of 640-730 nm.

2. An instrument as recited in claim 1, wherein the images are selected from the group consisting of: gray scale images; pseudo-colored images; and combinations of gray scale images and pseudo-color images.

3. An instrument as recited in claim 1, wherein the controller is further operative to optimize in vivo determination of a boundary of the tumor present in the region by presenting the spectrally-encoded images to a surgeon for determining surgical margins around the tumor based upon disruption in the collagen structure.

4. An instrument as recited in claim 1, wherein the illuminator includes a polarizer so that the images generated by the imaging detector are cross-polarized.

5. An instrument for imaging a region of tissue having a tumor to minimize an optical effect of melanin and hemoglobin, the instrument comprising:
 an illuminator for illuminating the region with a first wavelength of light and a second wavelength of light;
 an imaging detector for generating raw images of the region based upon the first wavelength of light and the second wavelength of light;
 a polarizer for creating cross-polarized images; and
 a controller connected to the imaging detector for receiving and storing the images, the controller being operative to spectrally encode a first cross-polarized raw image at the first wavelength of light with a second cross-polarized raw image at the second wavelength of light to create a corrected image,
wherein each of the images generated by the imaging detector includes a respective set of pixels, and wherein the controller is configured to spectrally encode the images by: (i) multiplying a cross-polarized image of a first wavelength of light by a first value to produce a first term, (ii) adding a cross-polarized image of a second wavelength of light to the first term to produce a combined image, and (iii) adding a second value to the combined image to produce the spectrally-encoded image,
wherein the first value is a normalizing value calculated from a mean pixel value of the cross-polarized image of the first wavelength of light and a mean pixel value of the cross-polarized image of the second wavelength of light;

wherein the second value is a normalizing value calculated from a mean pixel value of the cross-polarized image of the second wavelength of light and a mean pixel value of a subset of pixels of the cross-polarized image of the second wavelength of light, the subset corresponding to a non-tumor sub-region;

wherein the first and second wavelengths of light are selected from the group consisting of: approximately 440 nm light; approximately 550 nm light; approximately 590 nm light; approximately 640 nm light; light in a range of 410 nm to 440 nm; light in a range of 570 nm to 590 nm; and light in a range of 640-730 nm.

6. An instrument as recited in claim 5, wherein the non-tumor sub-region exhibits a higher pigmentation as compared to other image pixels.

7. An instrument as recited in claim 5, wherein the non-tumor sub-region exhibits a higher vascularization as compared to other image pixels.

8. An instrument as recited in claim 5, wherein the corrected image is presented in gray scale.

9. An instrument as recited in claim 5, wherein the corrected image is pseudo-colored.

10. An instrument as recited in claim 9, wherein: the pseudo-colored corrected image has pixels with normalized intensity of less than 40% corresponding to a maximal disruption of a collagen network of the region being colored black and purple; and pixels corresponding to normal collagen are represented with colors ranging from blue to white.

11. An instrument as recited in claim 5, wherein the controller is configured to present the corrected image for visual review by an operator to assess margins of the tumor based on examining a lateral spread of collagen disruption.

12. An instrument as recited in claim 5, wherein the controller is configured to apply a low pass filter to the raw images for reducing noise.

13. An instrument as recited in claim 5, wherein the first wavelength light is approximately 440 nm light and the second wavelength light is approximately 640 nm light.

14. An instrument for imaging a region of tissue to define margins of a tumor in the region, the instrument comprising:
 an illuminator for illuminating the region with at least two wavelengths of light;
 an imaging detector for generating images of the region based upon the at least two wavelengths of light; and
 a controller connected to the imaging detector for receiving and storing the images, and for creating a spectrally-encoded image to exclude effects of background, uneven pigmentation and vascularization for visualizing a collagen structure of the region of the tissue so that disruption of the collagen structure caused by the tumor is determined and, in turn, the margins of the tumor are determined,
wherein each of the images generated by the imaging detector includes a respective set of pixels, and wherein the controller is configured to create the spectrally-encode image by: (i) multiplying a cross-polarized image of a first wavelength by a first value to produce a first term, (ii) adding a cross-polarized image of a second wavelength to the first term to produce a combined image, and (iii) adding a second value to the combined image to produce the spectrally-encoded image,
wherein the first value is a normalizing value calculated from a mean pixel value of the cross-polarized image of the first wavelength and a mean pixel value of the cross-polarized image of the second wavelength;

wherein the second value is a normalizing value calculated from a mean pixel value of the cross-polarized image of the second wavelength and a mean pixel value of a subset of pixels of the cross-polarized image of the second wavelength, the subset corresponding to a non-tumor sub-region;

wherein the at least two wavelengths of light are selected from the group consisting of: approximately 440 nm light; approximately 550 nm light; approximately 590 nm light; approximately 640 nm light; light in a range of 410 nm to 440 nm; light in a range of 570 nm to 590 nm; and light in a range of 640-730 nm.

* * * * *